US009061062B2

(12) United States Patent
Gruell et al.

(10) Patent No.: US 9,061,062 B2
(45) Date of Patent: Jun. 23, 2015

(54) LIPIDOMIMETIC COMPOUNDS AND USES THEREOF

(75) Inventors: Holger Gruell, Eindhoven (NL); Sander Langereis, Mierlo (NL); Johan Lub, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 4 days.

(21) Appl. No.: 14/122,253

(22) PCT Filed: Jun. 6, 2012

(86) PCT No.: PCT/IB2012/052829
§ 371 (c)(1), (2), (4) Date: Nov. 26, 2013

(87) PCT Pub. No.: WO2012/172457
PCT Pub. Date: Dec. 20, 2012

(65) Prior Publication Data

US 2014/0127135 A1 May 8, 2014

(30) Foreign Application Priority Data

Jun. 16, 2011 (EP) .................................... 11170139

(51) Int. Cl.

| | |
|---|---|
| ***A61K 9/12*** | (2006.01) |
| ***A61K 49/18*** | (2006.01) |
| ***A61K 47/14*** | (2006.01) |
| ***C07C 69/28*** | (2006.01) |
| ***C07C 69/33*** | (2006.01) |
| ***C07C 69/708*** | (2006.01) |
| ***A61K 9/127*** | (2006.01) |
| ***A61K 41/00*** | (2006.01) |
| ***A61K 49/08*** | (2006.01) |
| ***A61K 49/10*** | (2006.01) |

(52) U.S. Cl.
CPC ................. *A61K 47/14* (2013.01); *C07C 69/28* (2013.01); *C07C 69/33* (2013.01); *C07C 69/708* (2013.01); *A61K 9/1273* (2013.01); *A61K 41/0028* (2013.01); *A61K 49/085* (2013.01); *A61K 49/10* (2013.01); *A61K 49/103* (2013.01); *A61K 49/106* (2013.01); *A61K 49/1812* (2013.01); *A61K 9/1272* (2013.01)

(58) Field of Classification Search
CPC ................................ A61K 9/12; A61K 49/18
USPC .......... 424/1.21, 9.3, 9.321, 450; 514/44, 227
See application file for complete search history.

(56) References Cited

U.S. PATENT DOCUMENTS 4,235,871 A 11/1980 Papahadjopoulos et al.
2003/0031704 A1* 2/2003 Huang et al. .................. 424/450

FOREIGN PATENT DOCUMENTS

WO 9614057 A 5/1996

OTHER PUBLICATIONS

Lindner L.H. et al. "Novel temperature-sensitive liposomes with prolonged circulation time". Clin Cancer Res. 2004;10:2168-78.

Torchilin, V.P. et al. "Liposomes: a practical approach", IRL Press, Oxford (1990), pp. 33-104.

Lasic, D.D., "Liposomes from physics to applications", Elsevier Science Publishers, Amsterdam, 1993.

Widder, K.J. "Liposomes", Marcel Dekker, Inc., New York (1983).

Terreno, E. et al. "From spherical to osmotically shrunken paramagnetic liposomes: An improved generation of LIPOCEST MRI agents with highly shifted water protons". Angew Chem Int. Ed. 46, 966-968 (2007).

Caravan, P. et al., "Gadolinium (III) chelates as MRI contrast agents: structure, dynamics and applications". Chem. Rev., 99, 2293-2352 (1999).

Peters, J.A. et al. "Lanthanide induced shifts and relaxation rate enhancements". Prog. Nucl. Magn. Reson. Spectr., 28, 283-350 (1999).

Aime, S. et al., "Highly sensitive MRI chemical exchange saturation transfer agents using liposomes".Angew, Chem. Int. Ed., 44, 5513-5515 (2005).

Terreno, E. et al. "Highly shifted LIPOCEST agents based on the encapsulation of neutral polynuclear paramagnetic shift reagents", Chemical Communications, Issue 5, 2008, pp. 600-602.

Lindner L.H. et al: Novel Temperature-Sensitive Liposomes with Prolonged Circulation Time, Clinical Cancer Research, the American Association for Cancer Research, US, vol. 10, No. 6, Mar. 15, 2004 pp. 2168-2179.

(Continued)

*Primary Examiner* — Michael G Hartley
*Assistant Examiner* — Jagadishwar Samala

(57) ABSTRACT

Disclosed are lipidomimetic compounds of formula I (I) wherein: G represents a group satisfying formula II: HO—$CH_2$—{CH(OH)—$CH_2$-0}$_m$-$CH_2$—{C(=0)-0-$CH_2$})$_q$— formula II each n independently is an integer from 1-30; m is an integer from 1-10; q is 0 or 1. These compounds can be added to the lipid bilayer of thermosensitive liposomes, for the purpose of aiding in the prevention of leakage of the liposomes' contents at 37° C., and retarding clearance from circulation.

(I)

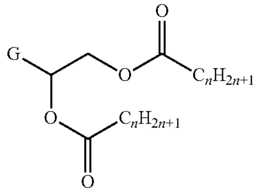

12 Claims, 3 Drawing Sheets

(56) References Cited

OTHER PUBLICATIONS

Yatvin, M.B. "Design of liposomes for enhanced local release of drugs by hperthermia". Science 1978, vol. 202, No. 4374, pp. 1290-1293.

Bratton, D.L. "Effects of platelet activating factor and related lipids on phase transition of dipalmitoylphosphatidylcholine". Biochimica Et Biophysica Acta 1988, 941, 76-82.

Needham, D. et al. "A New Temperature-sensitiv Liposome for use with Mild hyperthermia: characterization and testing in a human tumor xenograft model". Cancer Research 2000, 60, 1197-1201.

Kong, G. et al. "Efficacy of liposomes and hyperthermia in a human tumor xenograft model: importance of triggered drug release". Cancer Research 2000, 60(24), 6950-6957.

De Smet, M. et al. "Temperature-sensitive liposomes for doxorubicin delivery under MRI guidance". , H. Journal of Controlled Release 2010, Elndhoven, The Netherlands.

Hauck, M.L. et al "Phase I trial of doxorubicin-containing low temperature sensitive liposomes in spontaneous canine tumors". Clinical Cancer Research 2006, 12(13), 4004-4010.

Langereis, S. et al. "A temperature-sensitive liposomal 1H CEST and 19F contrast agent for MR image-guided drug delivery". J. Am. Chem. Soc. 2009;131:1380-1381.

D'Arrigo, P. et al. "Discriminationo fChain Positions in Mixed Short/Long-Chain Glycerophosphocholines by NMR Chemical Shift Variations". Journal of the Amercan Oil Chemists' Society, Nov. 2008, vol. 85, Issue 11, pp. 1005-1011.

Tokumura, A. et al. "Mass-Spectrometric Analyses of Biologically-Active Choline Phospholipids and Their Lyso Derivatives". 1983 Chemical & Pharmaceutical Bulletin 31 (12): 4425-4435.

* cited by examiner

LIPIDOMIMETIC COMPOUNDS AND USES THEREOF

CROSS-REFERENCE TO PRIOR APPLICATIONS

This application is the U.S. National Phase application under 35 U.S.C. §371 of International Application Ser. No. PCT/IB2012/052829, filed on Jun. 6, 2012, which claims the benefit of application Ser. No. 11170139.7, filed on Jun. 16, 2011. These applications are hereby incorporated by reference herein.

FIELD OF THE INVENTION

The invention is in the field of thermosensitive carriers for the targeted, local delivery of drugs or diagnostic agents. The invention relates to lipidomimetic compounds, and particularly pertains to carriers such as liposomes, suitable for the temperature-responsive release of materials contained therein, and to the localized delivery of drugs and/or imaging agents by means of temperature-responsive release carriers.

BACKGROUND OF THE INVENTION

Many diseases that are mostly localized in a certain tissue are treated with systemically administered drugs. A well-known example of standard cancer therapy is a systemic chemotherapy coming along with significant side effects for the patient due to undesired biodistribution and toxicity. The therapeutic window of these drugs is usually defined by the minimal required therapeutic concentration in the diseased tissue on the one hand, and the toxic effects in non-targeted organs, e.g. liver, spleen, on the other.

Localized treatment by, for example, local release of cytostatics from nanocarriers promises a more efficient treatment and a larger therapeutic window compared to standard therapeutics. Localized drug delivery is also important if other therapeutic options such as surgery are too risky as is often the case for liver cancers. Localized drug delivery can also become the preferred treatment option for many indications in cardiovascular disease (CVD), such as atherosclerosis in the coronary arteries.

Medical imaging technology, such as magnetic resonance imaging (MRI) or ultrasound imaging, can not only be used for treatment planning, but also to control local drug delivery under image guidance. Focused ultrasound is the method of choice to induce local drug delivery, since it offers several advantages. This technique is non-invasive, can be focused on the diseased tissue and shows only very limited adverse effects on the surrounding tissue. Ultrasound can provide two kinds of trigger for drug delivery. First, the target tissue can be heated in a controlled way with a precision of about half a degree centigrade in a temperature range from body temperature up to 100° C. Second, the ultrasound waves are strong pressure oscillations that provide a stimulus for drug delivery based on mechanical forces.

The skilled person faces several challenges in providing carrier systems for the release of materials such as drugs or imaging compounds. Thus, e.g., the carrier system needs to be designed such that it can be loaded with a sufficient amount of said materials. Particularly if the material to be released comprises drugs, the carrier system should be sensitive to an external stimulus, such as (local) changes in temperature or pressure which allow for quick and localized release of a drug. Moreover, the drug delivery process needs to be under full control, i.e. the drug release at the site of treatment must be measurable in vivo, the amount and rate of drug release should serve as an input parameter for the determination of the subsequent stimulus application, hence drug delivery could be controlled in an image-guided feedback loop.

A significant improvement in the efficacy of liposomal drug therapies can be obtained by triggering the release of drugs by means of an external stimulus. One approach to trigger the release of encapsulated molecules is the use of temperature-sensitive liposomes. 1 In this case, the release of the drug occurs above the melting phase transition temperature (Tm) of the liposome membrane. At Tm, structural changes in the lipid membrane occur as it transfers from a gel-like to the liquid state phase. This transition leads to a distinct increase in the permeability of the membrane for solutes and water. The incorporation of phosphatidylcholines, such as lyso-PC, acetylated MPPC, and platelet activation factor (PAF), in the bilayer of liposomes has a pronounced effect on the properties of the liposomes. In 1988, Bratton et al. demonstrated that these lipids can be utilized to decrease the Tm of dipalmitoylphosphatidylcholine (DPPC)-based liposomes.2 Needham et al. have designed low temperature-sensitive liposomes (LTSLs) composed of lyso-PC/DPPC/DPPE-PEG2000 that release encapsulated doxorubicin (ThermoDox®) in a matter of seconds in response to mild hyperthermic conditions (39-42° C.).3 The quick release of aqueous solutes from the interior of these temperature-sensitive systems at temperatures close to the Tm was ascribed to the formation of transient pores. These pores are thermodynamically stable in the presence of micelle-forming phospholipids, such as lyso-PC and PEGylated phospholipids. Moreover, the transient pore formation has been ascribed to the accumulation of lysolipids by lateral diffusion within the lipid bilayer. Preclinical experiments with lyso-PC (R═C15H31, FIG. 1) based LTSLs loaded with doxorubicin in combination with an externally applied regional temperature increase clearly showed an improved efficacy of temperature-induced drug delivery.3,4 Instead of relying on liposomal accumulation in the tumor, hyperthermia was applied during the first hour after injection of the temperature-sensitive liposomal formulation of doxorubicin. This cytostatic drug was rapidly released in the microvasculature of the tumor and subsequently taken up by the tumor cells. Although lyso-PC based LTSLs loaded with doxorubicin have been successfully applied for drug delivery in combination with needle-based RF ablation, the stability of the liposomal formulation in plasma at 37° C. is suboptimal, showing up to 40% release of doxorubicin in 1 hour.

In the field of thermosensitive carriers for the local delivery, in a subject, of therapeutic and/or diagnostic agents, a need exists for providing carriers that are capable of longer circulation times, less leakage of their active contents at normal human body temperature (37° C.), and slower clearance from the system.

A reference addressing the foregoing desire is Lars H. Lindner et al., Clinical Cancer Research, 2004, Volume 10, Issue 6, pages 2168-2178. Herein liposomes are prepared on the basis of a third component, in addition to DPPC (1,2-dipalmitoyl-sn-glycero-3-phosphocholine) and DSPC (1,2-distearoyl-sn-glycero-3-phosphocholine). Said third component is DPPGOG (1,2-dipalmitoyl-sn-glycero-3-phospho ceroglycerol). The resulting three-component liposomes exhibit less leakage at 37° C. and a slower clearance from circulation.

The solution presented by Lindner et al. results in structurally more complex liposomes, and is limited to phospholipids. It would be desired to provide a synthetic tool to obtain thermosensitive liposomes that show an at least similar performance in avoiding leakage at 37° C., and an at least equally slow clearance, yet on the basis of a less complex liposome structure. Moreover, it would be desired to provide a synthetic tool to provide thermosensitive liposomes exhibiting a still slower clearance than the liposomes disclosed by Linder et al.

SUMMARY OF THE INVENTION

In order to better address the aforementioned desires, in one aspect, the invention presents a compound of formula I, formula I

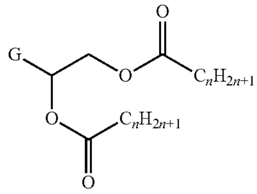

wherein:

G represents a group satisfying formula II:

$$HO—CH_2—\{CH(OH)—CH_2—O\}_m—CH_2—\{C(=O)—O—CH_2\}_q— \quad \text{formula II}$$

each n independently is an integer from 1-30;

m is an integer from 1-10;

q is 0 or 1.

In another aspect, the invention relates to a thermosensitive carrier comprising a lipid bilayer shell enclosing a cavity, wherein the lipid bilayer comprises one or more compounds as defined above.

In a further aspect, the invention is the use of a compound of formula I as defined above, as an additive to a lipid bilayer shell of a thermosensitive carrier.

In a still further aspect, a thermosensitive carrier is presented for the local administration of a therapeutic or diagnostic agent, said carrier comprising a lipid bilayer shell enclosing a cavity, said shell and/or said cavity comprising the agent, wherein the lipid bilayer comprises a compound of formula I as defined above.

In yet another aspect, the invention relates to any of the foregoing carriers for use in the in vivo release of a substance contained therein, respectively to treatment and imaging methods comprising administering any of the foregoing carriers to an animal, preferably a human, and affecting the in vivo release of a substance contained therein.

DETAILED DESCRIPTION OF THE INVENTION

Figure 1:
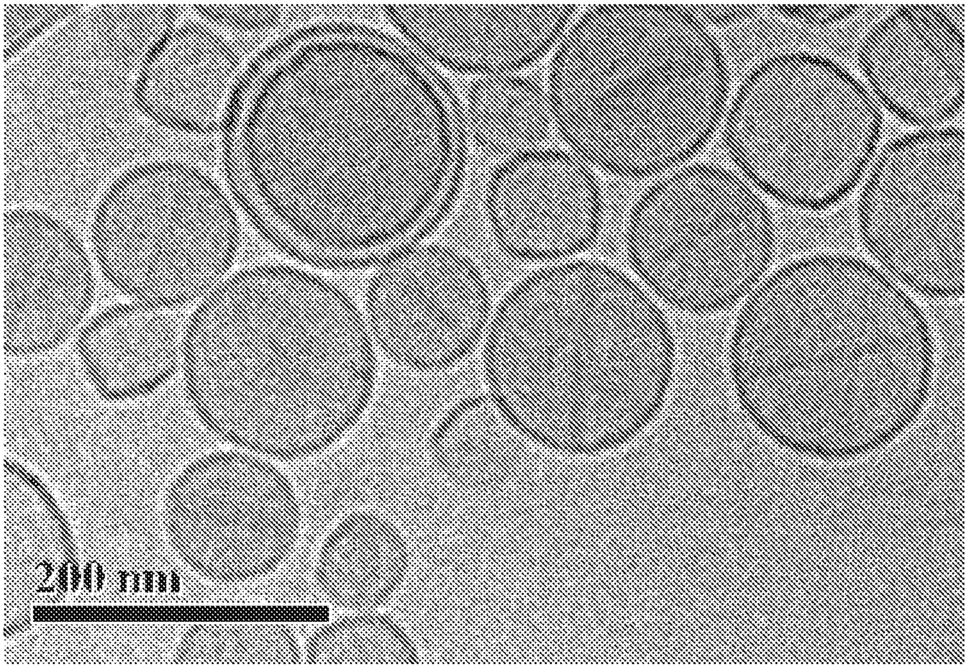
FIG. 1 shows a Cryo TEM image of temperature-sensitive liposomes containing $1_{15,3}$ (mentioned below) in the lipid bilayer and doxorubicin and [Gd(HPDO3A)($H_2O$)] in the aqueous lumen.
Figure 2:
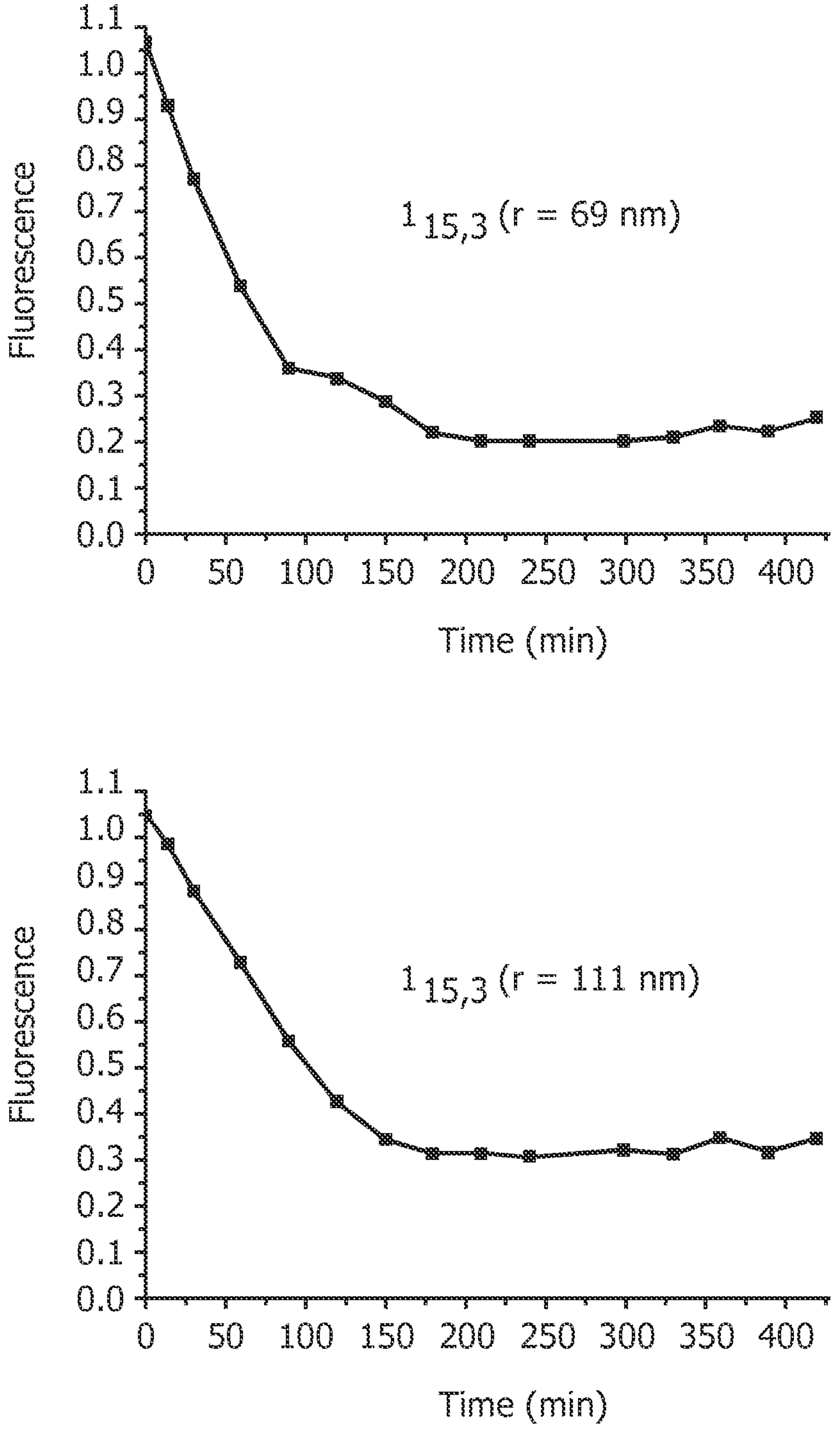
FIG. 2 presents graphs showing the encapsulation of doxorubicin in the lumen of the TSL containing $1_{15,3}$ over time.
Figure 3:
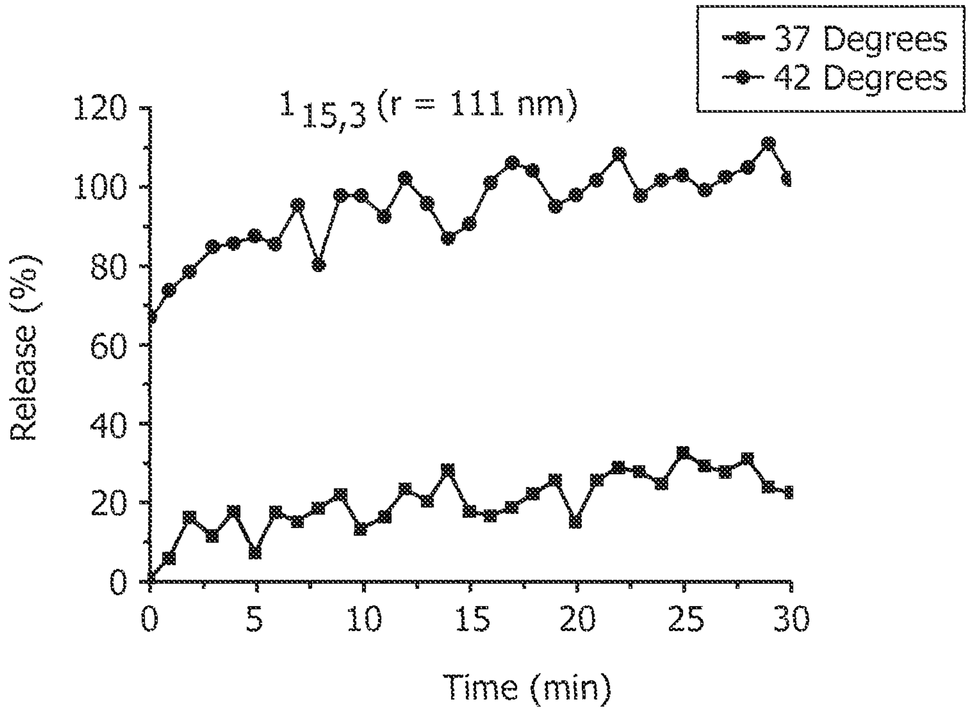
FIG. 3 is a graph for a TSL containing $1_{15,\ 3}$ in 50% fetal bovine serum (FBS) at 37° C. and 42° C. showing the release of doxorubicin at elevated temperatures.
Figure 4:
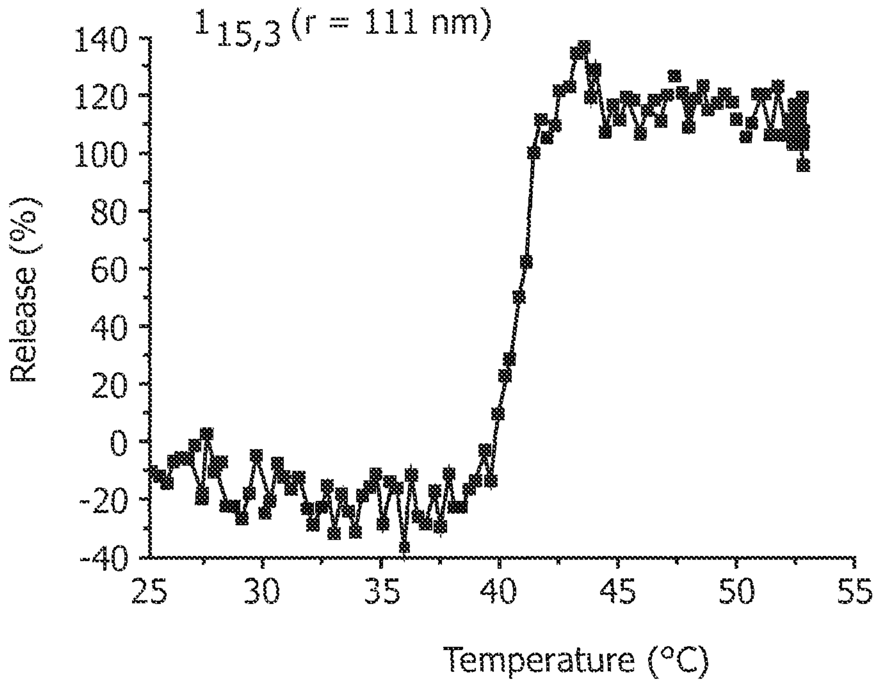
FIG. 4 shows the fluorescence of TSLs containing $1_{15,3}$ in 50% FBS during a linear temperature increase from 25° C. to 55° C. (heating ramp 0.5° C./min).

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention relates to carriers comprising a lipid bilayer shell. Particularly, such shells enclose a cavity, and are semipermeable, typically comprising phospholipids. The carriers include microcarriers, having a particle size of the order of a diameter of several to tens of microns, and nanocarriers, having a particle size of the order of tens to hundredths of nanometers. In the context of the invention, the carriers are hereinafter referred to as liposomes.

Liposomes are generally spherical vesicles comprising a bilayer membrane enclosing a cavity, or lumen. The bilayer can be made up of at least one phospholipid and may or may not comprise cholesterol. Liposomes can be composed of naturally-derived phospholipids with mixed lipid chains (like egg phosphatidylethanolamine), or of pure surfactant components like dioleoylphosphatidylethanolamine (DOPE). The term liposomes, as used in the description of the invention, includes lipid spheres usually denoted micelles.

A typical example of a semipermeable shell is also found in semipermeable membranes comprising a phospholipid bilayer. A phospholipid bilayer is the most permeable to small, uncharged solutes. Liposomes can be made on the basis of a phospholipid bilayer.

In a broad sense, the invention is based on the judicious insight to provide, rather than a further phospholipid component that becomes a constituent part of the lipid bilayer of a liposome, a lipidomimetic compound that can be separately incorporated into the lipid bilayer. The compounds particularly can be mixed into the lipid bilayer of a thermosensitive carrier such as a thermosensitive liposome, with the effect of prolonging the circulation time of the carrier.

Lipidomimetic Compounds

The invention, in one aspect, pertains to the lipidomimetic compounds themselves. These compounds satisfy formula (I) above. Preferably, the compounds are selected from the group consisting of the below compounds of formula III, formula IV, and combinations thereof.

formula III

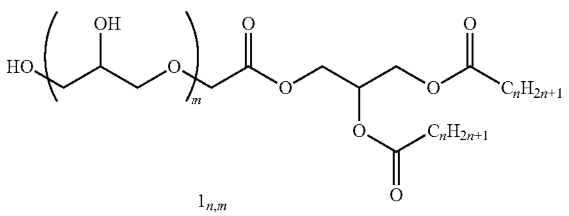

$1_{n,m}$ formula IV

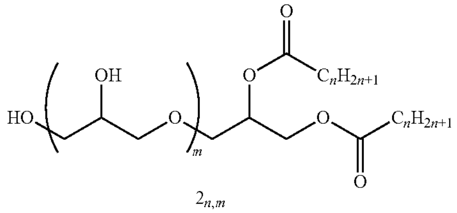

$2_{n,m}$

Herein, the integers m and n have the aforementioned meaning. Preferably, m is 2-6, more preferably 2-4 and most preferably 2 or, 3. Preferably each n independently is 8-24, more preferably each n independently is 12-18, and most preferably each n independently is 13, 15, or 17.

In a preferred embodiment, the compound satisfies formula V below, formula V

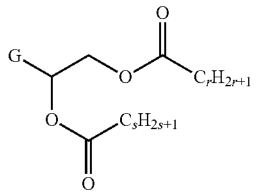

wherein G has the aforementioned meaning and r and s each independently are integers from 1-30 and the difference (r-s) is relatively small, i.e. below 10, preferably 0 to 5, and more preferably 1-3.

The compounds of the invention can be incorporated into the lipid bilayer of a thermosensitive carrier. They are generally incorporated by mixing them into the lipids of which the carriers are made. They are preferably present in a mole percentage of from 5 to 50 of the lipid bilayer, preferably 10%-30%.

The incorporation of the lipidomimetic compounds of the invention in the phospholipid bilayer of a thermosensitive liposome, allows rapid and quantitative release of drugs at a pre-defined temperature. This temperature-induced transition can also be utilized to release incorporated imaging probes (e.g. $T_1$, $T_2$, CEST MRI contrast agents) upon heating. Moreover, the incorporation of lipidomimetics can be utilized to tune the transmembrane water exchange rate in order to maximize the MR contrast enhancement between body temperature and hyperthermia, which is important in the field of MR image-guided drug delivery. Furthermore, the lipidomimetics do not exhibit a charge, which will positively influence the zeta potential of the liposomes, as a result of which the zeta potential is less negative than is the case with lipids comprising a phosphate group as in Linder et al.

The resulting liposomes are capable of showing a similar long or even longer circulation behaviour as the aforementioned liposomes based on DPPGOG.

Phospholipids

Preferred lipid bilayers (which can be made of lipids in general) are based on phospholipids.

Phospholipids are known and generally refer to phosphatidylcholine, phosphatidyl-ethanolamine, phosphatidylserine and phosphatidyl-inositol. In the invention it is preferred to employ phosphatidylcholine.

Thermosensitive Carriers

The invention concerns carriers that are thermosensitive. This means that the physical or chemical state of the carrier is dependent on its temperature.

Any thermosensitive carrier that can package a molecule of interest and that is intact at body temperature (i.e. 37° C.) but destroyed at any other, non-body temperature that can be tolerated by a subject may be used. Carriers of the invention include but are not limited to thermosensitive micro- and nanoparticles, thermosensitive polymersomes, thermosensitive liposomes, thermosensitive nanovesicles and thermosensitive nanospheres.

Thermosensitive nanovesicles generally have a diameter of up to 100 nm. In the context of this invention, vesicles larger than 100 nm, typically up to 5000 nm, are considered as microvesicles. The word vesicle describes any type of micro- or nanovesicle. Vesicles, such as liposomal vesicles, typically include a cavity which may contain any substance of interest. In the invention this is preferred, as outlined above.

Thermosensitive polymersomes include but are not limited to any polymer vesicle, including microvesicles and nanovesicles.

Thermosensitive liposomes include but are not limited to any liposome, including those having a prolonged half-life, e.g. PEGylated liposomes.

Thermosensitive liposomes for use in the invention ideally retain their structure at about 37°, i.e. human body temperature, but are destroyed at a higher temperature, preferably only slightly elevated above human body temperature, and preferably also above pyrexic body temperature. Typically about 42° C. is a highly useful temperature for thermally guided drug delivery.

The required heat to raise the temperature of the thermosensitive drug carriers so as to promote the destruction of the thermosensitive carriers may be used. Heat can be applied in any physiologically acceptable way, preferably by using a focused energy source capable of inducing highly localized hyperthermia. The energy can be provided through, e.g., microwaves, ultrasound, magnetic induction, infrared or light energy.

Thermosensitive liposomes are known in the art. Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic, D. D., Liposomes from physics to applications, Elsevier Science Publishers, Amsterdam, 1993; Liposomes, Marcel Dekker, Inc., New York (1983).

Entrapment of a drug or other substance within liposomes of the present invention may also be carried out using any conventional method in the art. In preparing liposome compositions of the present invention, stabilizers such as antioxidants and other additives may be used as long as they do not interfere substantially with the purpose of the invention.

Drug Carriers

In one aspect, the invention relates to a carrier suitable for the localized delivery of a biologically active agent, such as a drug. Hereinafter, the term "biologically active agent" will be referred to, in short, as "drug" and the carrier as a "drug carrier." A drug carrier in the context of the present invention refers to any material in or on which a bio-active agent can be contained so as to be capable of being released in the body of a subject.

The drug carrier is to be introduced into the body of a person to be subjected to MRI. This will be e.g. by injection in the blood stream, or by other methods to introduce the carrier into body fluid.

A drug is a chemical substance used in the treatment, cure, prevention, or diagnosis of a disease or disorder, or used to otherwise enhance physical or mental well-being. The guided delivery foreseen with the present invention will mostly be useful therapeutic agents (i.e. drugs in a strict sense, intended for therapy or prevention of diseases or disorders), but also for agents that are administered for diagnostic purposes. Although other bio-active agents, i.e. those that are not therapeutic or diagnostic, such as functional food ingredients, will not generally be subjected to guided and/or monitored delivery, such could be done using the present invention if desired.

The most optimal use of the invention is attained in the case of targeted therapeutics, i.e. drugs that are intended for targeted delivery, as such delivery will by nature benefit most from the monitoring made available by the invention. This pertains, e.g., to agents in the treatment of tumors to be delivered on site, to agents in the treatment or prevention of cardiovascular disorders, such as atherosclerosis in the coronary arteries, or to antithrombotic agents (e.g. for locally resolving blood cloths) or agents that require passing the blood-brain barrier such as neuromodulators as can be used in the treatment of neural conditions such as epilepsy, Alzheimer's disease, Parkinson's disease, or stroke. Benefits from the guidance and monitoring of targeted drug delivery are also applicable to targeted diagnostic agents. Similarly as with targeted therapeutics, here too cancer is an area where site-specific delivery can be of importance.

Bio-active agents suitable for use in the present invention include biologically active agents including therapeutic drugs, endogenous molecules, and pharmacologically active agents, including antibodies; nutritional molecules; cosmetic agents; diagnostic agents; and additional contrast agents for imaging. As used herein, an active agent includes pharmacologically acceptable salts of active agents.

The drug carriers of the present invention can comprise either hydrophilic or hydrophobic bioactive agents. A hydrophilic bioactive agent could be encapsulated in the aqueous compartment of the carrier, whereas hydrophobic bioactive agents could be incorporated in hydrophobic domains of the carrier, for instance in the lipid bilayer of liposomes. Nucleic acids, carbohydrates and, in general, proteins and peptides are water soluble or hydrophilic. For instance, bioactive agents which are small molecules, lipids, lipopolysaccharides, polynucleotides and antisense nucleotides (gene therapy agents) are also envisaged. Such biologically active agents, which may be incorporated, thus include non-peptide, non-protein drugs. It is possible within the scope of the present invention to incorporate drugs of a polymeric nature, but also to incorporate drugs of a relatively small molecular weight of less than 1500 g/mol, or even less than 500 g/mol.

Accordingly, compounds envisaged for use as bioactive agents in the context of the present invention include any compound with therapeutic or prophylactic effects. It can be a compound that affects or participates in tissue growth, cell growth, cell differentiation, a compound that is able to invoke a biological action such as an immune response, or a compound that can play any other role in one or more biological processes. A non-limiting list of examples includes antimicrobial agents (including antibacterial, antiviral agents and anti-fungal agents), anti-viral agents, anti-tumor agents, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, anti metabolites, antiproliferatives (including anti-angiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, ACE inhibitors, free radical scavengers, chelators, antioxidants, anti polymerases, and photodynamic therapy agents.

Relatively small peptides may be referred to by the number of amino acids (e.g. di-, tri-, tetrapeptides). A peptide with a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterised by the so called quaternary structure, a conglomerate of a number of polypeptides that are not necessarily chemically linked by amide bonds but are bonded by forces generally known to the skilled professional, such as electrostatic forces and Vanderwaals forces. The term peptides, proteins or mixtures thereof as used herein is to include all above mentioned possibilities.

Usually, the protein and/or peptide are selected on the basis of its biological activity. Depending on the type of polymer chosen, the product obtainable by the present process is highly suitable for controlled release of proteins and peptides. In a particular embodiment, the protein or peptide is a growth factor.

Other examples of peptides or proteins or entities comprising peptides or proteins, which may advantageously be contained in the loaded polymer include, but are not limited to, immunogenic peptides or immunogenic proteins, which include, but are not limited to, the following:

Toxins such as diphtheria toxin and tetanus toxin.

Viral surface antigens or parts of viruses such as adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus.

Bacterial surface antigens or parts of bacteria such as *Bordetella pertussis, Helicobacter pylori, Clostridium tetani, Corynebacterium diphtheria, Escherichia coli, Haemophilus influenza, Klebsiella species, Legionella pneumophila, Mycobacterium bovis, Mycobacterium leprae, Mycrobacterium tuberculosis, Neisseria gonorrhoeae, Neisseria meningitidis, Proteus species, Pseudomonas aeruginosa, Salmonella species, Shigella species, Staphylococcus aureus, Streptococcus pyogenes, Vibrio cholera* and *Yersinia pestis.*

Surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), *Stronglyloides duodenale* (hookworm), *Ancyclostoma duodenale* (hookworm), *Necator americanus* (hookworm), *Wucheria bancrofti* (filariasis), *Brugia malaya* (filariasis), *Loa loa* (filariasis), *Dipetalonema perstaris* (filariasis), *Dracuncula medinensis* (filariasis), and *Onchocerca volvulus* (filariasis).

Immunoglobulins such as IgG, IgA, IgM, Antirabies immunoglobulin, and Antivaccinia immunoglobulin.

Antitoxin such as Botulinum antitoxin, diphtheria antitoxin, gas gangrene antitoxin, tetanus antitoxin.

Antigens which elicit an immune response against foot and mouth disease.

Hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

Examples of other proteins or peptides are albumin, atrial natriuretic factor, renin, superoxide dismutase, alpha 1-antitrypsin, lung surfactant proteins, bacitracin, bestatin, cyclosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH and metkephamid.

Anti-tumor agents such as altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin and paclitaxel.

Antimicrobial agents comprising:

Antibiotics such as ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, and cephalexin. Aminoglycosides such as amikacin, neomycin, dibekacyn, kanamycin, gentamycin, netilmycin, tobramycin. Macrolides such as amphotericin B, novobiocin, bacitracin, nystatin, clindamycin, polymyxins, colistin, rovamycin, erythromycin, spectinomycin, lincomycin, vancomycin Tetracyclines such as chlortetracycline, oxytetracycline, demeclocycline, rolitetracycline, doxycycline, tetracycline and minocycline. Other antibiotics such as chloramphenicol, rifamycin, rifampicin and thiamphenicol.

Chemotherapeutic agents such as the sulfonamides sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole and trimethoprim with sulfamethoxazole or sulfametrole.

Urinary tract antiseptics such as methanamine, quinolones (norfloxacin, cinoxacin), nalidixic acid, nitro-compounds (nitrofurantoine, nifurtoinol) and oxolinic acid.

Drug for anaerobic infections such as metronidazole.

Drugs for tuberculosis such as aminosalicyclic acid, isoniazide, cycloserine, rifampicine, ethambutol, tiocarlide, ethionamide and viomycin.

Drugs for leprosy such as amithiozone, rifampicine, clofazimine, sodium sulfoxone and diaminodiphenylsulfone (DDS, dapsone).

Antifungal agents such as amphotericin B, ketoconazole, clotrimazole, miconazole, econazole, natamycin, flucytosine, nystatine and griseofulvin.

Antiviral agents such as aciclovir, idoxuridine, amantidine, methisazone, cytarabine, vidarabine and ganciclovir.

Chemotherapy of amebiasis such as chloroquine, iodoquinol, clioquinol, metronidazole, dehydroemetine, paromomycin, diloxanide, furoatetimidazole and emetine.

Anti-malarial agents such as chloroquine, pyrimethamine, hydroxychloroquine, quinine, mefloquine, sulfadoxine/pyrimethamine, pentamidine, sodium suramin, primaquine, trimethoprim and proguanil.

Anti-helminthiasis agents such as antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Anti-inflammatory agents such as acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen and tolmetin.

Anti-gout agents such as colchicine and allopurinol.

Centrally acting (opoid) analgesics such as alfentanil, methadone, bezitramide, morphine, buprenorfine, nicomorphine, butorfanol, pentazocine, codeine, pethidine, dextromoramide, piritranide, dextropropoxyphene, sufentanil and fentanyl.

Local anesthetics such as articaine, mepivacaine, bupivacaine, prilocalne, etidocaine, procaine, lidocaine and tetracaine.

Drugs for Parkinson's disease such as amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide and trihexyphenidyl.

Centrally active muscle relaxants such as baclofen, carisoprodol, chlormezanone, chlorzoxazone, cyclobenzaprine, dantrolene, diazepam, febarbamate, mefenoxalone, mephenesin, metoxalone, methocarbamol and tolperisone.

Corticosteroids comprising:

Mineralocorticosteroids such as cortisol, desoxycorticosterone and fluorohydrocortisone.

Glucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide).

Androgens comprising:

Androgenic steroids used in therapy such as danazole, fluoxymesterone, mesterolone, methyltestosterone, testosterone and salts thereof.

Anabolic steroids used in therapy such as calusterone, nandrolone and salts thereof, dromostanolone, oxandrolone, ethylestrenol, oxymetholone, methandriol, stanozolol methandrostenolone and testolactone.

Antiandrogens such as cyproterone acetate.

Estrogens comprising estrogenic steroids used in therapy such as diethylstilbestrol, estradiol, estriol, ethinylestradiol, mestranol and quinestrol.

Anti-estrogens such as chlorotrianisene, clomiphene, ethamoxytriphetol, nafoxidine and tamoxifen.

Progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

Thyroid drugs comprising:

Thyroid drugs used in therapy such as levothyronine and liothyronine

Anti-thyroid drugs used in therapy such as carbimazole, methimazole, methylthiouracil and propylthiouracil.

Apart from bioactive agents which are water soluble, other water-soluble compounds can be incorporated such as anti-oxidants, ions, chelating agents, dyes, imaging compounds.

Preferred therapeutic agents are in the area of cancer (e.g. antitumor) and cardiovascular disease.

Methods of preparing lipophilic drug derivatives which are suitable for nanoparticle or liposome formulation are known in the art (see e.g., U.S. Pat. No. 5,534,499 describing covalent attachment of therapeutic agents to a fatty acid chain of a phospholipid). Drugs in the present invention can also be prodrugs.

The drug may be present in the inner, the outer, or both of the compartments of the carrier, e.g. in the cavity and/or in the shell of a liposome. The distribution of the drug is independent of the distribution of any other agents comprised in the drug carrier, such as a paramagnetic chemical shift reagent or a paramagnetic agent. A combination of drugs may be used and any of these drugs may be present in the inner, the outer, or both of the compartments of the drug carrier, e.g. in the cavity and/or in the shell of a liposome.

Imaging Agents

In another aspect, the invention relates to carriers that are suitable as imaging agents, preferably for MRI. To this end, the carrier comprises (in the cavity, in the shell, or on the surface thereof) a substance capable of inducing contrast enhancement. These substances include $T_1$ and/or $T_2$ contrast enhancers as well as CEST MRI contrast enhancers.

Almost all current MRI scans are based on the imaging of bulk water molecules, which are present at a very high concentration throughout the whole body in all tissues. If the contrast between different tissues is insufficient to obtain clinical information, MRI contrast agents (CAs), such as low molecular weight complexes of gadolinium, are administered. These paramagnetic complexes reduce the longitudinal ($T_1$) and transverse relaxation times ($T_2$) of the protons of water molecules. Also manganese acts as a $T_1$ contrast agent. The carrier can comprise contrast enhancers for $^1$H MRI, for $^{19}$F MRI, or both. In the invention also an all-in-one concept can be realized of $^{19}$F MRI in combination with $T_1$, $T_2$, and preferably also with CEST contrast, in $^1$H MRI.

CEST MRI

The invention, in a preferred embodiment, also relates to CEST MRI contrast enhancement. This method serves to generate image contrast by utilizing Chemical Exchange-dependent Saturation Transfer (CEST) from selected, magnetically pre-saturated protons to the bulk water molecules determined by MRI.

If used in CEST MRI, preferred carriers of the invention, i.e. the thermosensitive carriers that have a semipermeable shell enclosing a cavity, contribute to an optimal CEST contrast enhancement. For, the advantage of these carriers is that the CEST contrast enhancement can be conducted on the basis of a paramagnetic chemical shift agent contained in the cavity, in interaction with a pool of protons or other MRI analytes also present in the cavity.

Although the invention, in this preferred embodiment, relates to the application of any CEST-type contrast enhancement to thermosensitive drug release, it is preferred to make use of more advanced CEST methods as have become available.

CEST in combination with a paramagnetic chemical shift reagent (ParaCEST) is a method, in which the magnetization of a pool of paramagnetically shifted protons of a CEST contrast agent is selectively saturated by the application of radio frequency (RF) radiation. The transfer of this saturation to bulk water molecules by proton exchange leads to a reduced amount of excitable water protons in the environment of the CEST contrast agent. Thus a decrease of the bulk water signal intensity is observed, which can be used to create a (negative) contrast enhancement in MRI images.

An approach to obtain a high CEST efficiency is based on utilizing the large number of water molecules of a solution containing a paramagnetic shift reagent (e.g. Na[Tm(dotma)($H_2O$)]), wherein "$H_4$dotma" stands for α,α',α",α'"-tetramethyl-1,4,7,10-tetraacetic acid and dotma represents the respective fourfold deprotonated tetraanionic form of the ligand, to provide a pool of protons that are chemically shifted and that, therefore, can selectively be saturated by an RF pulse. If this system is encapsulated in a carrier, e.g. a liposome, the magnetic saturation can be transferred to the bulk water molecules at the outside of the carriers, which are not chemically shifted (LipoCEST). The amount of magnetization transfer and hence the extent of contrast enhancement are determined by the rate of the diffusion of water through the shell of the carrier, e.g. a phospholipid membrane, as well as by the amount of water within the carrier.

The optimum water exchange rate is directly correlated with the chemical shift difference between the proton pool inside of the carrier and the bulk water outside of the carrier. The paramagnetic shift that is induced on the water molecules inside the liposomes consists of two main contributions: chemical shift resulting from a direct dipolar interaction between the water molecules and the shift reagent ($\delta_{dip}$), and chemical shift caused by a bulk magnetic susceptibility effect ($\delta_{bms}$). The overall paramagnetic shift is the sum of these two contributions:

$$\delta=\delta_{dip}+\delta_{bms} \quad (1)$$

$\delta_{bms}$ is zero for spherical particles, but it can be significant for anisotropic particles. The aspherical particles experience a force in a magnetic field, which causes them to align with the magnetic field lines. In the case of liposomes, this effect is further increased, if they bear paramagnetic molecules associated with the phospholipid membrane.

A reference on CEST using aspherical liposomes is Terreno, E. et al. *Angew. Chem. Int. Ed.* 46, 966-968 (2007).

In the invention, a paramagnetic shift reagent can be comprised in any manner in or on the carrier. It is preferred to have the shift reagent in sufficient interaction with a pool of protons by comprising both the reagent and the pool in the cavity of the carrier.

The paramagnetic chemical shift reagent or reagents can basically be any paramagnetic agent suitable to render the relatively large number of water molecules of a solution or dispersion in which it is contained, into a pool of protons that are chemically shifted regarding their MR resonance frequency, with respect to the surrounding protons of the bulk water molecules. As the liposomes comprise a shell that fundamentally allows exchange of protons with their direct environment, the saturation caused by a selective RF pulse will be transferred to the environment of the loaded thermosensitive drug carriers. Thus, upon conducting magnetic resonance imaging, the direct environment of the thermosensitive drug carriers will show a decreased signal intensity as compared to other bulk water molecules, and thus allows to detect the direct environment of the contrast agents due to a decreased signal intensity. The paramagnetic chemical shift reagent is to comprise a paramagnetic compound, i.e. any compound having paramagnetic properties. Preferably the paramagnetic compound comprises a paramagnetic metal ions, e.g. metal ions complexed by chelate ligands. Paramagnetic metal ions are known to the skilled person, and do not require elucidation here. E.g., early and late transition metals, explicitly including chromium, manganese, iron, as well as lanthanides, such as gadolinium, europium, dysprosium, holmium, erbium, thulium, ytterbium.

The paramagnetic chemical shift reagent is to comprise a chelating structure capable of strongly binding to the paramagnetic metal and allowing the metal to interact with water, or with another suitable source of protons. With respect to suitable chelating structures, reference is made to P. Caravan et al., Chem. Rev., 99, 2293-2352 (1999). Preferably the water is at least transiently coordinated to the metal of the paramagnetic reagent. With respect to paramagnetic shift mechanisms, reference is made to J. A. Peters et al., Prog. Nucl. Magn. Reson. Spectr., 28, 283-350 (1999). In one embodiment, the chelating structure itself also comprises exchangeable protons, e.g. hydroxyl, amine, or amide protons.

Suitably, the paramagnetic chemical shift reagent comprises a lanthanide ion coordinated with a chelating structure, e.g. macrocylic lanthanide(III) chelates derived from 1,4,7,10-tetraazacyclododecane-1,4,7,10-tetraacetic acid ($H_4$ dota), 1,4,7,10-tetraazacyclododecane-α,α',α",α'"-tetramethyl-1,4,7,10-tetraacetic acid ($H_4$dotma), and related ligands that allow for an axially coordinated water molecule in the paramagnetic reagent. In this respect reference is made to Aime et al., Angew. Chem. Int. Ed., 44, 5513-5515 (2005). A number of the same, similar or different chelating units may be combined in a dendrimeric or polymeric structure providing dendritic or polymeric chemical shift reagents. A general advantage of using dendritic or polymeric paramagnetic compounds is that high effective concentrations of the paramagnetic metal complex can be achieved, without increasing the osmolarity of the solution as much as it would be the case when using mononuclear paramagnetic compounds. Here reference is made to E. Terreno, A. Barge, L. Beltrami, G. Cravotto, D. D. Castelli, F. Fedeli, B. Jebasingh, S. Aime, *Chemical Communications,* 2008, 600-602.

Preferably, the paramagnetic chemical shift reagent is water-soluble. Suitable chemical shift reagents are known to the person skilled in the art. The CEST contrast agents do not require any specific chemical shift reagent, as long as the shift reagent and the pool of protons have a sufficient interaction to result in a pool of chemically shifted protons.

Preferably, the paramagnetic shift reagent is a metal complex comprising a metal ion and a ligand that is based on a multidentate chelate ligand. More preferably, the interaction of the chemical shift reagent with the pool of protons is provided in the form of coordination. Thus it is preferred for the metal complex to have at least one coordination site of the metal left open for the coordination of at least one water molecule.

Examples of suitable water-soluble chemical shift reagents are $[Ln(hpdo3a)(H_2O)]$ (1), $[Ln(dota)(H_2O)]^-$ (2), $[Ln(dotma)(H_2O)]^-$ (3), $[Ln(dotam)(H_2O)]^{3+}$ (4), and $[Ln(dtpa)(H_2O)]^{2-}$ (5), including derivatives thereof and related compounds, with Ln being a lanthanide ion.

Preferably the paramagnetic chemical shift reagent is a lanthanide complex such as in formulae 1-5 below:

1

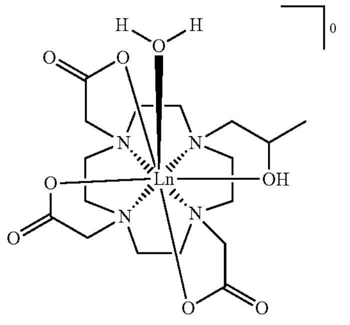

$[Ln(hpdo3a)(H_2O)]$

2

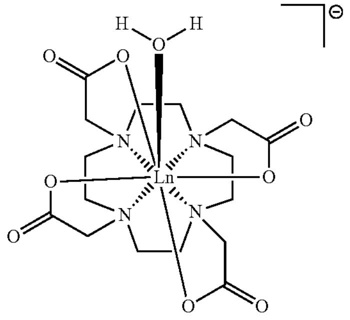

$[Ln(dota)(H_2O)]^-$

3

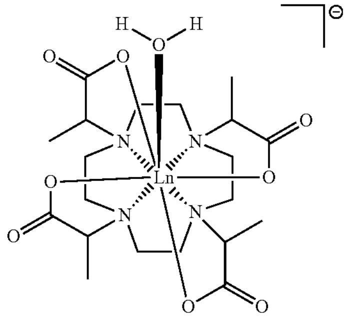

$[Ln(dotma)(H_2O)]^-$

4

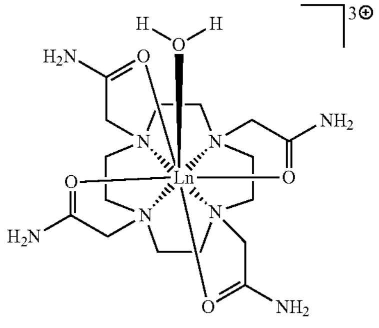

$[Ln(dotam)(H_2O)]^{3+}$

-continued

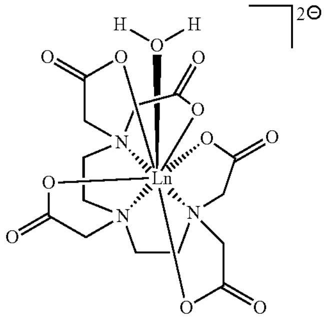

$[Ln(dtpa)(H_2O)]^{2-}$ wherein the lanthanide is $Eu^{3+}$, $Dy^{3+}$, $Ho^{3+}$, $Er^{3+}$, $Tm^{3+}$, $Yb^{3+}$, and preferably is $Tm^{3+}$ or $Dy^{3+}$.

The paramagnetic chemical shift reagent is typically comprised in the agent in an amount of from 1 mM to 2000 mM, preferably of from 10 mM to 1000 mM, and more preferably of from 50 mM to 200 mM.

The foregoing metal-containing compounds may be dissolved, emulsified, suspended or in any other form distributed homogeneously or inhomogeneously in the cavity, i.e. the inner compartment of the liposome. It may alternatively be linked to the outer compartment of the liposome by at least one covalent or non-covalent bond, or any combination of those. Furthermore the same or at least one different metal-containing compound may be present simultaneously in any of the compartments.

It can be envisaged that the paramagnetic agent and the drug are one and the same, if the drug itself comprises an appropriate metal.

Further contrast enhancement agents

The contrast agents of the invention may comprise $T_1$, $T_2$ or $T_2$* reducing agents. In this respect reference is made to Aime et al., *Journal of the American Chemical Society,* 2007, 129, 2430-2431. Also, an all-in-one concept can be realized of $T_1$, $T_2$ or $T_2$* and CEST contrast agents.

The chemical shift difference between the internal and the bulk water protons of the thermosensitive drug carriers, can be further enhanced by providing the thermosensitive drug carrier's membrane with a further paramagnetic agent, which is not necessarily a chemical shift reagent. Thus, the orientation of the aspherical carrier in the magnetic field is affected and the aforementioned bulk susceptibility effect is enhanced. The further paramagnetic agent is preferably an amphiphilic compound comprising a lanthanide complex (on the more polar side of the amphiphilic compound), and having an apolar tail which has a tendency to preferably integrate in and align with the lipid bilayer at the thermosensitive drug carrier's surface based on hydrophobic molecular interactions. These amphiphilic paramagnetic complexes can e.g. be:

6

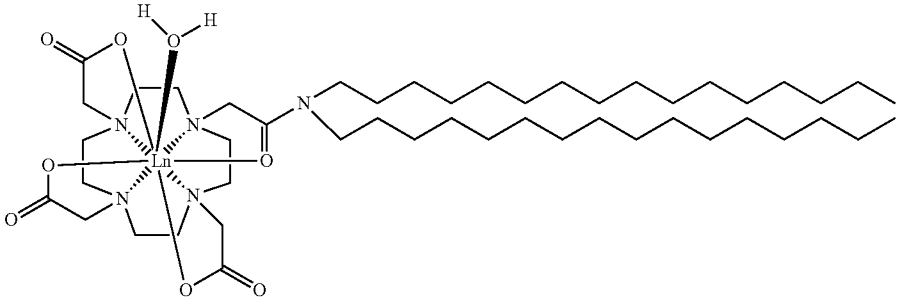

7

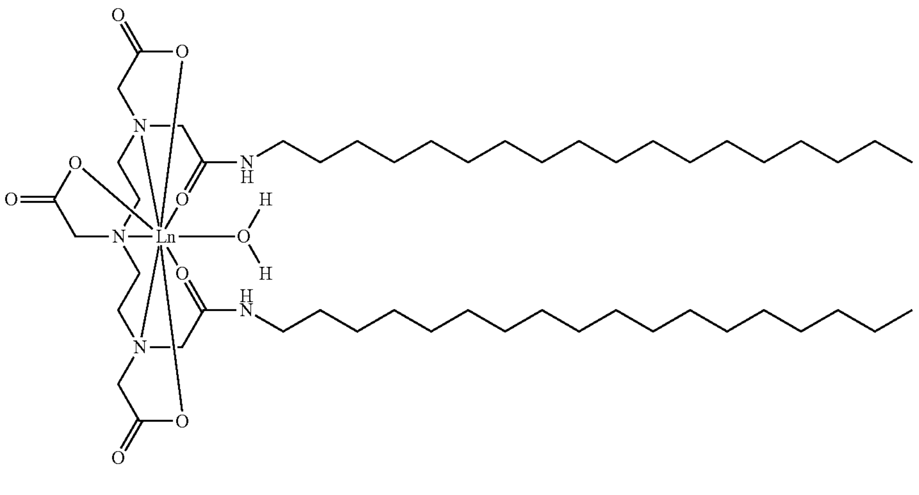

-continued

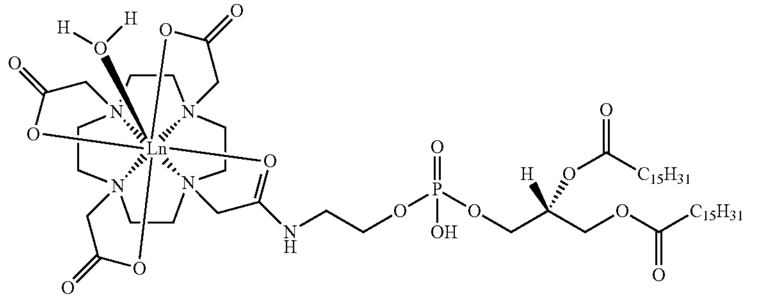

8

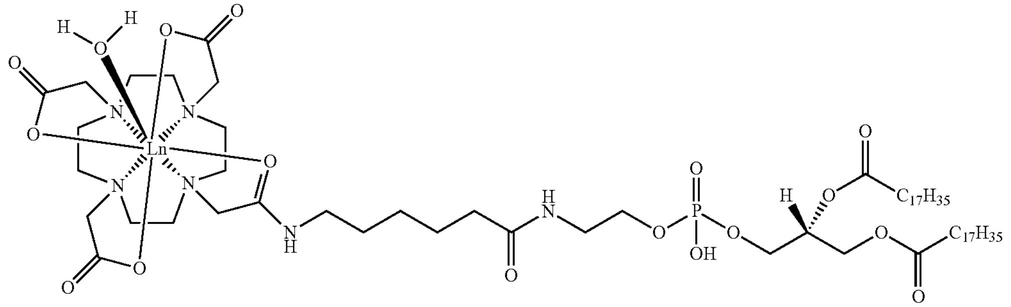

9

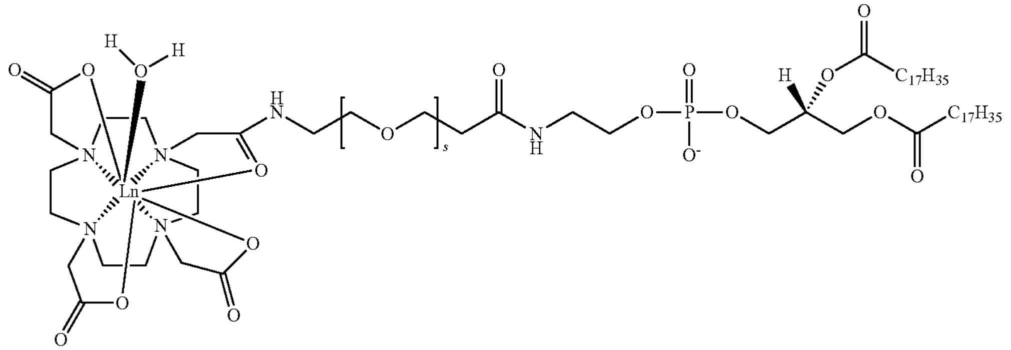

10

Combined $^{19}F$ and $^{1}H$ MR Contrast Enhancement

With the invention a suitable combination of $^{19}F$ and $^{1}H$ MR can be realized in various ways.

Thus, a dual or multiple-label MR contrast can be generated by utilizing a CEST mechanism and/or $^{19}F$ MR. Alternatively, multiple MR contrasts may be generated through the modification of the longitudinal relaxation time ($T_1$), or the transverse relaxation time ($T_2$) of the imaged analyte (typically the protons of water) by a metal-containing compound present in the carrier. Any of these contrast enhancing mechanisms may further be used in any combination thereof.

The dual/multiple labeled MRI contrast, depending on the physical state of the carrier, is monitored either in a subsequent or interleaved manner with conventional MR equipment—or simultaneously, using sequence combinations on dual-tuned spectrometer systems e.g. at $^{1}H$ and $^{19}F$ MR resonance frequencies.

In this respect the invention also relates to the use of simultaneous dual nuclei MR imaging in monitoring and/or guiding drug delivery.

The combination of a CEST and a $^{19}F$ contrast agent in a thermo-sensitive liposome offers the opportunity to monitor the drug release process independently and simultaneously by means of CEST and $^{19}F$ MRI. Simultaneous monitoring of the two different MR signals is mediated by corresponding dual-label MR techniques. This approach leads to several possible advantages. Thus, the spatial distribution of the drug-loaded particles can be assessed prior to drug release by means of CEST MRI; the $^{1}H$ CEST and the $^{19}F$ MR signals scale with the amount of released drug, which allows for quantitative control of the delivered drug dose in vivo using a feedback loop; the release of drugs from the carrier at the diseased site can be induced by a local stimulus, such as heating in the case of thermosensitive liposomes using e.g. RF or ultrasound; the CEST MR contrast enhancement can be switched on and off at will.

$^{19}F$ MRI Contrast Agents

MR detectable $^{19}F$ does not naturally occur in the body, i.e. $^{19}F$ MRI will thus be necessarily based on the use of added $^{19}F$ contrast agents.

Contrast agents for $^{19}F$ MRI preferably have a large number of magnetically equivalent fluoro-groups (the sensitivity scales linearly with the number of magnetically equivalent F atoms per molecule). With a view to the desired combination with CEST MRI, the $^{19}F$ MR contrast agents used are preferably water-soluble, and particularly are preferably charged molecules so as to have as high a water-solubility as possible. With a view to application in phospholipid shells, the preferred $^{19}F$ contrast agents do not significantly bind, or are not significantly associated with phospholipids. With a view to their release in the human or animal body, the $^{19}F$ contrast agents are preferably of low toxicity and high biocompatibility.

Preferred $^{19}F$ contrast agents are charged per-F analogs of aliphatic hydrocarbons.

The invention will be illustrated with reference to the following, non-limiting examples and the accompanying non-limiting Figures.

EXAMPLE 1

Synthesis of (2S)-9,13,17,18-tetrahydroxy-5-oxo-4,7,11,15-tetraoxaoctadecane-1,2-diyl dipalmitate $1_{15,3}$. See scheme 1

Scheme 1: synthetic route towards (2S)-9,13,17,18-tetrahydroxy-5-oxo-4,7,11,15-tetraoctadecane-1,2-diyl dipalmitate $1_{15,3}$.

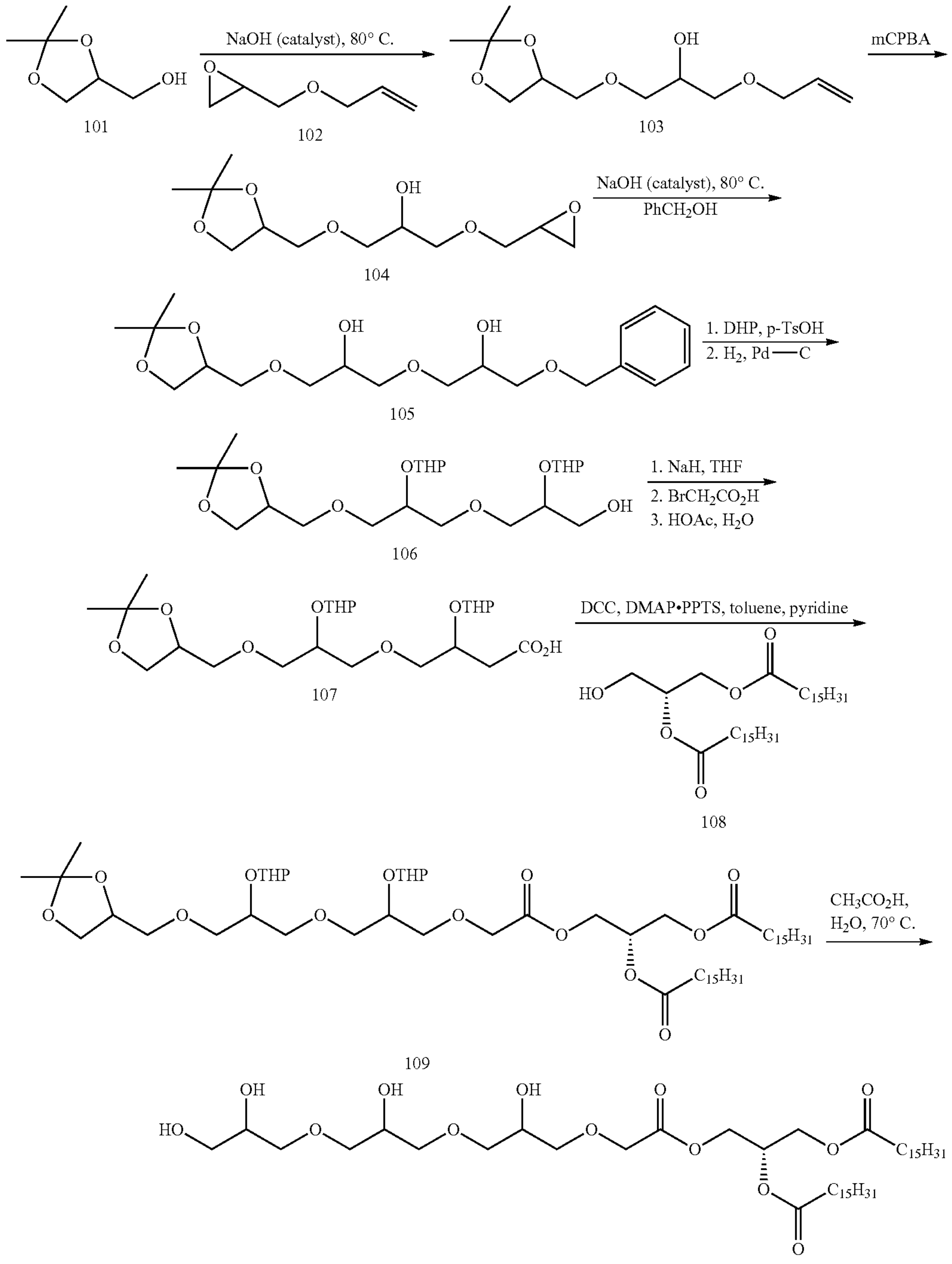

101 102 103

104

105

106

107 108

109

$1_{15,3}$

Triester $1_{15,3}$ was made by esterification of (R)-3-hydroxypropane-1,2-diyl dipalmitate (108) with acid derivative 107 followed by acidic deprotection of intermediate triester 109. Acid derivative 107 is a derivative of triglycerol of which the backbone of the glycerol units were introduced by the addition of solketal (101) to 2-((allyloxy)methyl)oxirane (102). Product 103 obtained in this way was oxidised to epoxide 104 and the epoxide ring was opened by benzylalcohol to form 105. After protection of the remaining hydroxyl groups as tetrahydropyranyl ether in 10 and removal of the benzylic group alcohol 106 was obtained that was converted in acid derivative 107 by reaction with bromoacetic acid.

EXAMPLE 2

Synthesis of 3-(3-(2,3-dihydroxypropoxy)-2-hydroxypropoxy)propane-1,2-diyl distearate ($2_{17,2}$) see scheme 2

EXAMPLE 3

Temperature-sensitive liposomes containing lipidomimetics ($1_{n,R}$) have been engineered for the triggered release of MRI contrast agents, such as [Gd(hpdo3a)($H_2O$)], and drugs, such as doxorubicin. Temperature-sensitive liposomal formulations were prepared composed of DPPC:DSPC: $1_{15,3}$=50:20:30 (molar ratio). The lipids were dissolved in a solution of chloroform/methanol (4:1 v/v) and the solvent was evaporated under reduced pressure until a thin and homogenous lipid film was formed, which was further dried overnight under a nitrogen flow. Hydration of the film was performed at 60° C. with a 120 mM $(NH_4)_2SO_4$ buffer (pH=5.4) containing 250 mM [Gd(HPDO3A)($H_2O$)]. The suspension was extruded at 60° C. through a 400 nm filter (2 times), 200 nm filter (2 times) and 100 nm filter (5 times). After extrusion, the extraliposomal buffer (containing [Gd (HPDO3A)($H_2O$)]) was replaced by HEPES Buffered Saline Scheme 2: Synthesis of 3-(3-(2,3-dihydroxypropoxy)-2-hydroxypropoxy)propane-1,2-diyl distearate ($2_{17,2}$)

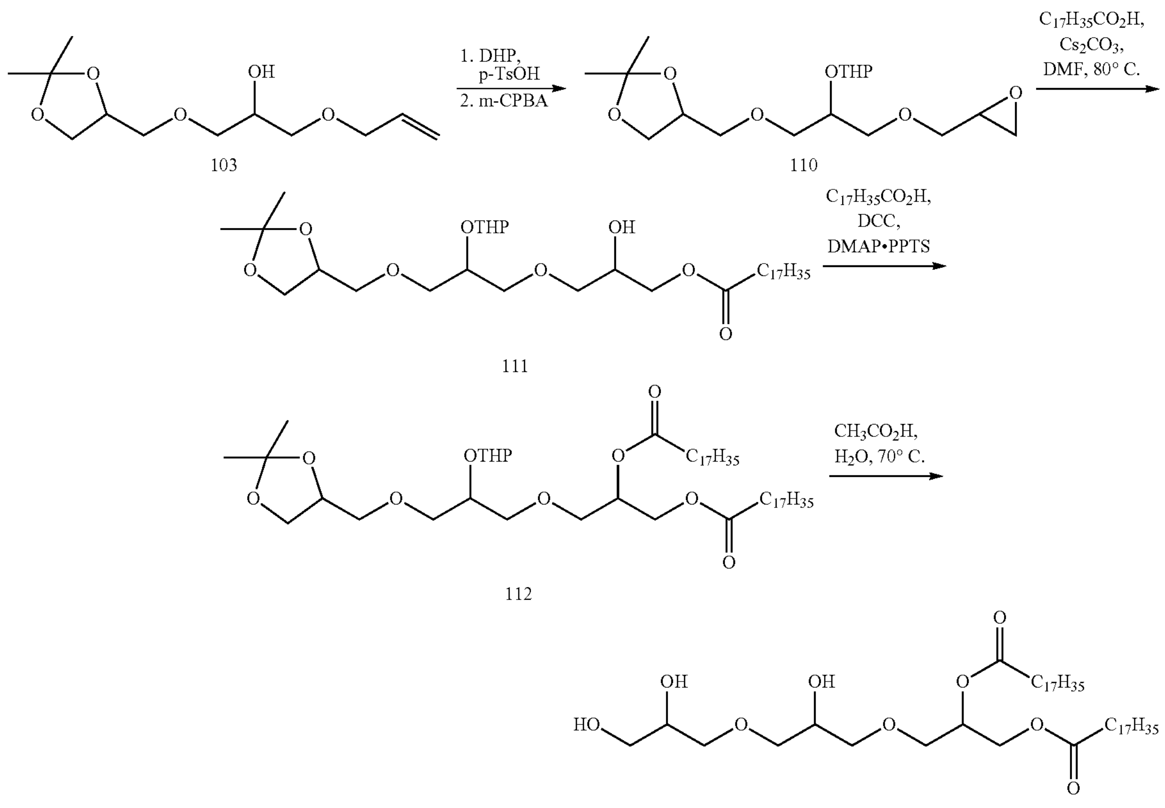

103

110

111

112

$2_{17,2}$

Product 103 containing the backbone to form a triglycerol derivative was made as shown in scheme 1. After protection of the hydroxyl group as a tetrahydropyranyl ether and epoxidation of the allyl group, compound 110 was obtained of which the epoxide ring was opened by cesium stearate to form mono ester 111. After esterification of the remaining hydroxyl group of 111 with stearic acid followed by deprotection with acid, product $2_{17,2}$ was obtained.

(HBS), pH 7.4 (20 mM HEPES, 137 mM NaCl) by gel filtration through a PD-10 column (GE Healthcare). DOX solution in HBS (5 mg/mL) was added to the liposomes at a 20:1 phospholipid to DOX weight ratio and incubated at 37° C. After the incubation, the extraliposomal DOX was removed by passing the liposomes through another PD-10 column. The $T_m$ and the hydrodynamic diameter of the liposomes were determined by differential scanning calorimetry (DSC) and dynamic light scattering (DLS), respectively. The liposomes containing $1_{15,3}$ in their lipid bilayer displayed a hydrodynamic radius of 111 nm (after extrusion through a 200 nm PC filter) and a $T_m$ of 41.9° C.

The invention claimed is:

1. A compound satisfying structural formula I formula I

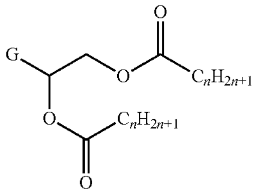

wherein:

G represents a group satisfying formula II:

$$HO—CH_2—\{CH(OH)—CH_2—O\}_m—CH_2—\{C(=O)—O—CH_2\}_q—$$ formula II each n independently is an integer from 1-30;

m is an integer from 2-10;

q is 0 or 1.

2. A compound according to claim 1, selected from the group consisting of the below compounds of formula III, formula IV, and combinations thereof formula III

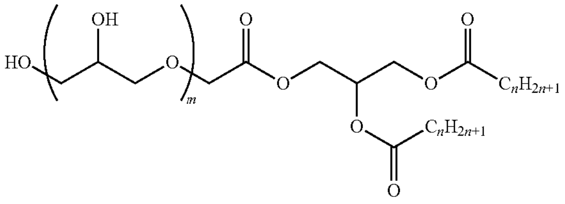

$1_{n,m}$ formula IV

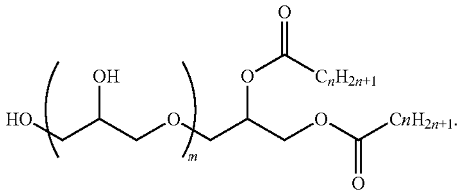

$2_{n,m}$

3. A compound according to claim 1, wherein m is 2-6, preferably 2 or 3.

4. A compound according to claim 1, wherein each n independently is 12-18, preferably 13, 15, or 17.

5. A thermosensitive carrier comprising a lipid bilayer shell enclosing a cavity, wherein the lipid bilayer comprises one or more compounds as defined in claim 1.

6. A thermosensitive carrier according to claim 5, comprising an active agent selected from the group consisting of therapeutic agents, imaging agents, and combinations thereof.

7. A thermosensitive carrier according to claim 5, for use in the in vivo release of a substance contained therein, respectively to treatment and imaging methods comprising administering any of the foregoing carriers to an animal, preferably a human, and affecting the in vivo release of a substance contained therein.

8. A drug delivery system comprising a carrier as defined in claim 5, and at least one drug substance.

9. An imaging system comprising a carrier as defined in claim 5, and at least one MRI contrast enhancing substance.

10. A combined system for imaged drug delivery, comprising a carrier as defined in claim 5, at least one drug substance, and at least one MRI contrast enhancing substance.

11. The compound as defined in claim 1 for uses, as an additive to a lipid bilayer shell of a thermosensitive carrier.

12. A compound, satisfying formula V formula V

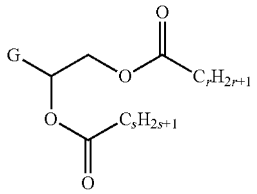

wherein

G represents a group satisfying formula II:

$$HO—CH_2—\{CH(OH)—CH_2—O\}_m—CH_2—\{C(=O)—O—CH_2\}_q—$$ formula II m is an integer from 2-10;

q is 0 or 1, and wherein r and s each independently are integers from 1-30 and the difference (r-s) is 1 to 5, more preferably 1-3.

* * * * *